United States Patent
Kim et al.

(10) Patent No.: US 9,040,572 B2
(45) Date of Patent: May 26, 2015

(54) METHOD OF PREPARING BENZOIMIDAZOLE DERIVATIVES

(75) Inventors: In Woo Kim, Seongnam-si (KR); Ji Duck Kim, Yongin-si (KR); Hong Chul Yoon, Incheon (KR); Hee Kyoon Yoon, Cheongju-si (KR); Byung Goo Lee, Suwon-si (KR); Joon Hwan Lee, Yongin-si (KR); Young Mook Lim, Gwangju-si (KR); Soo Jin Choi, Yongin-si (KR)

(73) Assignee: Daewoong Pharmaceutical Co., Ltd., Seoul (KR)

( * ) Notice: Subject to any disclaimer, the term of this patent is extended or adjusted under 35 U.S.C. 154(b) by 0 days.

(21) Appl. No.: 13/821,067

(22) PCT Filed: Sep. 27, 2011

(86) PCT No.: PCT/KR2011/007109
§ 371 (c)(1),
(2), (4) Date: May 14, 2013

(87) PCT Pub. No.: WO2012/044043
PCT Pub. Date: Apr. 5, 2012

(65) Prior Publication Data
US 2013/0231477 A1    Sep. 5, 2013

(30) Foreign Application Priority Data
Sep. 28, 2010  (KR) .................. 10-2010-0093818

(51) Int. Cl.
| | | |
|---|---|---|
| C07D 401/14 | (2006.01) | |
| C07D 235/18 | (2006.01) | |
| C07D 471/04 | (2006.01) | |
| C07D 401/10 | (2006.01) | |
| C07D 413/14 | (2006.01) | |
| C07B 37/04 | (2006.01) | |

(52) U.S. Cl.
CPC .............. *C07D 401/10* (2013.01); *C07B 37/04* (2013.01); *C07D 235/18* (2013.01); *C07D 401/14* (2013.01); *C07D 413/14* (2013.01); *C07D 471/04* (2013.01)

(58) Field of Classification Search
USPC .......................................... 514/394; 546/345
See application file for complete search history.

(56) References Cited

U.S. PATENT DOCUMENTS

| 7,271,261 B2 * | 9/2007 | Arienti et al. ................. 544/139 |
| 7,582,657 B2 * | 9/2009 | Chen et al. ................... 514/336 |
| 2009/0018124 A1 * | 1/2009 | Kim et al. ................. 514/228.2 |

FOREIGN PATENT DOCUMENTS

| JP | 2005-506349 | 3/2005 |
| JP | 2009-542802 | 12/2009 |
| WO | WO 2004/011439 A2 | 2/2004 |
| WO | WO 2004/016611 | 2/2004 |
| WO | WO 2004/035533 A1 | 4/2004 |
| WO | WO 2006/080821 A1 | 8/2006 |
| WO | WO 2009/129625 | 10/2009 |

OTHER PUBLICATIONS

Joule; Heterocyclic Chemistry, 2010, Fifth Ed, Wiley, pp. 507-508.*
Katritzky; "Comprehensive Organic Functional Group Transformations II" 2005 vol. III p. 103.*
Chida; Chemistry Letters, 1988, 969-972.*
Sun; Bioorganic & Medicinal Chemistry Letters 8 (1998) 361-364.*
Vijaykumar; Bioorganic & Medicinal Chemistry Letters 16 (2006) 3829-3832.*
Punji; Journal of Molecular Catalysis A: Chemical 259 (2006) 78-83.*
Harapanhalli; J. Med. Chem. 1996, 39, 4804-4809.*
Verner; J. Med. Chem. 2001, 44, 2753-2771.*
Park, H.G., et al., "Biarylcarboxybenzamide derivatives as potent vanilloid receptor (VR1) antagonistic ligands," Bioorganic & Medicinal Chemistry Letters, vol. 15, No. 3, pp. 631-634, (2005).
PCT/KR2011/007109 International Search Report and Written Opinion mailed Mar. 26, 2012.
Ben-Alloum et al. "Benzimidazoles: Oxydation Heterocyclisante par le Nitrobenzene ou le Dimethylsulfoxyde sur Silice et sous Irradiation Micro-ondes ou Ultra-violet" Tetrahedron Letters, 1998, vol. 39, pp. 4481-4484.
EP11829549.2 Extended European Search Report issued on Apr. 17, 2014.
CN201180050309.6 First Office Action issued Nov. 5, 2013.
Mao, et al. "Research Progress in the Synthesis of Benzimidazoles" Chinese Journal of Organic Chemistry, 28(3), 542-547 (2008).
Trahanovsky et al., "Controlled Oxidation of Organic Compounds with Cerium (IV). II. The Oxidation of Toluenes" Journal of Organic Chemistry 31(6), (1966), 2033-2035.
JP Application No. 2013-531482 Office Action Dated Jun. 3, 2014.

* cited by examiner

*Primary Examiner* — John Mabry
*Assistant Examiner* — Daniel Carcanague
(74) *Attorney, Agent, or Firm* — McNees Wallace & Nurick LLC

(57) ABSTRACT

This invention relates to a method of preparing a benzoimidazole derivative at high purity and high yield so as to enable the production of the benzoimidazole derivative compound as an antagonist against a vanilloid reactor-1, and particularly to a method of preparing a benzoimidazole derivative at high purity and high yield, wherein the benzoimidazole derivative is synthesized using a novel intermediate, namely, benzaldehyde, and thereby the preparation process is simple so that it can be applied to production.

18 Claims, No Drawings

METHOD OF PREPARING BENZOIMIDAZOLE DERIVATIVES

RELATED APPLICATIONS

This application is the National Stage Entry of International Application No. PCT/KR2011/007109 filed on Sep. 27, 2011, which claims priority to Korean Application No. 10-2010-0093818 filed on Sep. 28, 2010, both of which are incorporated herein by reference in their entireties.

TECHNICAL FIELD

The present invention relates to a novel method of preparing a benzoimidazole derivative which exhibits efficacy as an antagonist of a vanilloid receptor (a capsaicin receptor; Transient Receptor Potential Channel, Vanilloid subfamily member 1; TRPV-1; Vanilloid receptor-1; VR-1), and to an intermediate thereof and a method of preparing the intermediate.

BACKGROUND ART

A vanilloid receptor that is a benzoimidazole derivative according to the present invention has always been assumed to be a receptor of capsaicin (trans-8-methyl-N-vanilyl-6-noneneamide) which is the active component of chili peppers. By Caterina et al. in 1997, the above receptor was cloned, which is called the vanilloid receptor subtype 1 (hereinafter referred to as "VR-1") (Caterina et al., Nature, 1997, 389, 816). VR-1 which is distributed in fine unmyelinated neurons (C-fibers) and thin myelinated neurons (A-fibers) in the human body is activated from external or internal stimuli so that cations such as calcium, sodium, etc., are intensively introduced into the terminals of nerve fibers, and is thus known to be an ion channel capable of responding to pain stimuli. The external stimuli that activate VR-1 are reported to include heat stimuli or noxious stimuli by acids, as well as vanilloid compounds (Tominaga et al., Neuron, 1998, 21, 531), and the internal stimuli are known to be leukotriene metabolites such as 12-hydroperoxyeicosatetraenoic acid (12-HPETE) (Hwang at al., PNAS, 2000, 97, 3655) and arachidonic acid derivatives such as anandamide (Premkumar et al., Nature, 2000, 408, 985).

Based on such physiological actions, VR-1 has received attention as an integrated regulator that plays an important role in transmitting a variety of external noxious stimuli into nerve cells in vivo. Recently, a knockout mouse from which VR-1 genes was removed was produced (Caterina et al., Science, 2000, 288, 306), and its pain reaction was not greatly different from that of a normal mouse with respect to general stimuli, but was considerably reduced with respect to heat stimuli, heat hyperalgesia, etc., thereby confirming the importance of VR-1 with respect to noxious stimuli.

VR-1 is mainly expressed in primary sensory neurons in vivo (Caterina et al., Nature, 1997, 389, 816), and these sensory neurons are essential to regulating functions of internal organs of the human body, including the skin, bone tissue, bladder, gastrointestinal tract, lung, etc. In addition, VR-1 is considered to be important in regulating cell division or cell signals while being distributed throughout the entire body or the other nerve cells including the central nervous system, kidney, stomach, or T-cells (Nozawa et al., Neuroscience Letter, 2001, 309, 33; Yiangou et al., Lancet (North America Edition), 2001, 357, 1338; Birder et al., PNAS, 2001, 98, 13396).

In regard thereto, diseases based on the regulation of VR-1 activity include pain, acute pain, chronic pain, neuropathatic pain, pain after operations, migraine, arthralgia, neuropathy, nerve injury, diabetic neuropathy, neuropathic disease, neurodermatitis, stroke, overactive bladder, irritable bowel syndrome, a respiratory problem such as asthma, chronic obstructive pulmonary disease, etc., stimuli of the skin, eye, and mucous membrane, pruritus, fever, gastric-duodenal ulcer, inflammatory bowel disease or inflammatory disease and urgency urinary incontinence (KR Patent Publication No. 10-2004-0034804), anti-obesity effects (Pharmacol. Rev., 1986, 38, 179), etc.

Both the VR-1 agonist and antagonist in terms of pharmaceutical mechanisms may be used to treat the diseases as mentioned above. The pharmaceutical mechanism responsible for the alleviation effect of pain by the VR1 agonist is based on desensitization of capsaicin-sensitive sensory neurons. Specifically, pain and stimulation of the sensory neuron desensitizes the nerve cell, thereby preventing pain from occurring due to other noxious stimuli. Because of the initial pain, the VR-1 agonist is limitedly developed now as a topical therapeutic agent. In contrast, the VR-1 antagonist has a mechanism that blocks the recognition of a pain signal of the sensory neuron and thus does not cause any initial pain and does not cause any stimulation, and is thereby mainly studied as a treatment intended to treat systemic disease.

Meanwhile, as a known method of preparing a benzoimidazole derivative, Korean Patent Publication No. 10-2007-0113207 discloses a variety of benzoimidazoles as the VR-1 antagonist and a method of preparing the same, wherein a benzoic acid derivative is synthesized and subjected to amidation with a diamine derivative and then to cyclization to benzoimidazole. However, this method is problematic in undesirably increasing the amount of impurities and the cost and decreasing the purity, making it difficult to apply it to production because the preparation process includes a two-step cyclization.

Therefore, the present inventors have studied conventional methods of preparing benzoimidazole derivatives and discovered that when benzaldehyde is used as an intermediate instead of a benzoic acid derivative conventionally used, the reaction may become simple, the need for an expensive reagent may be obviated, the yield may increase and the amount of impurities may decrease, thereby culminating in the present invention.

DISCLOSURE OF INVENTION

Technical Problem

Accordingly, the present invention is intended to provide a novel method of preparing a benzoimidazole derivative, in which the reaction is simple, the need for an expensive reagent is obviated, in which the yield may increase and the amount of impurities may decrease, and also to provide a novel intermediate.

Solution to Problem

An aspect of the present invention provides a method of preparing a compound represented by Chemical Formula 1 as shown in Scheme 1 below.

[Scheme 1]

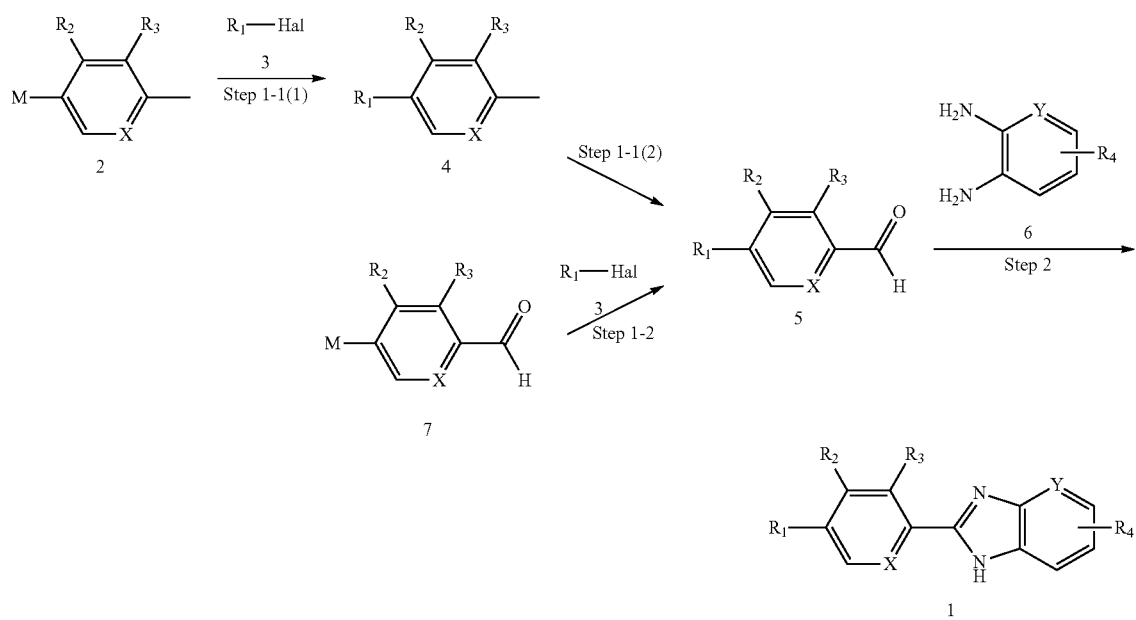

wherein M is B(OH)$_2$, B(i-Pr)$_2$, Sn(CH$_3$)$_3$, or SnBu$_3$,
X is CH or N,
Y is CR$_5$ or N,

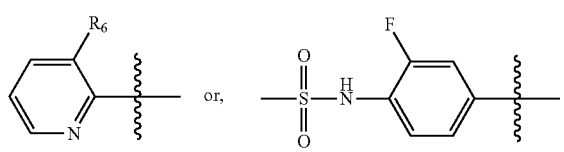

R$_2$ and R$_3$ each are hydrogen or R$_2$ and R$_3$ together form a benzene ring, R$_4$ is halogen, unsubstituted or halogen-substituted C$_{1-5}$ alkyl, or morpholino, and preferably Br, C(CH$_3$)$_3$, CF$_3$ or morpholino, R$_5$ is hydrogen, halogen, or unsubstituted or halogen-substituted C$_{1-3}$ alkyl, and preferably hydrogen, Br, Cl or CF$_3$, and R$_6$ is hydrogen, halogen, or unsubstituted or halogen-substituted C$_{1-3}$ alkyl, and preferably Cl or CF$_3$.

In Chemical Formula 1, R$_4$ is substituted at position 5, 6 or 7 of a benzimidazole structure as shown below.

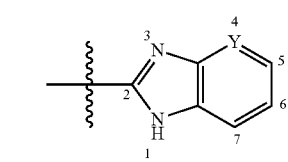

Also, as benzimidazole may be present as a tautomer depending on the position of substitution of hydrogen at positions 1 and 3, Chemical Formula 1 may be provided in the form of a tautomer as represented below.

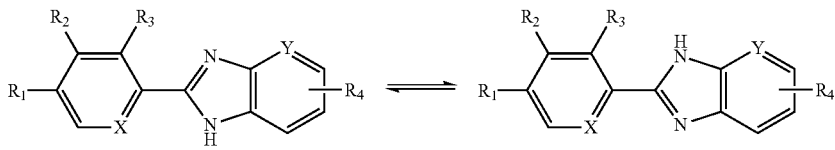

Specifically, the compound represented by Chemical Formula 1 is any one selected from the group consisting of:
1) 6-tert-butyl-2-(4-(3-chloropyridin-2-yl)phenyl)-1H-benzo[d]imidazole,
2) 6-tert-butyl-2-(4-(3-chloropyridin-2-yl)naphthalen-1-yl)-1H-benzo[d]imidazole,
3) N-(4'-(4,6-bis(trifluoromethyl)-1H-benzo[d]imidazol-2-yl)-3-fluorobiphenyl-4-yl) methanesulfoneamide,
4) 4-bromo-6-(trifluoromethyl)-2-(4-(3-(trifluoromethyl)pyridin-2-yl)phenyl)-1H-benzo[d]imidazole,
5) 6-bromo-2-(4-(3-(trifluoromethyl)pyridin-2-yl)phenyl)-1H-imidazo[4,5-b]pyridine,
6) 6-(trifluoromethyl)-2-(3-(trifluoromethyl)-2,3'-bipyridin-6'-yl)-1H-benzo[d]imidazole,
7) 6-bromo-2-(3-(trifluoromethyl)-2,3'-bipyridin-6'-yl)-1H-benzo[d]imidazole, 8) 6-bromo-2-(3-(trifluoromethyl)-2,3'-bipyridin-6'-yl)-1H-imidazo[4,5-b]pyridine,
9) 4-(2-(3-(trifluoromethyl)-2,3'-bipyridin-6'-yl)-3H-benzo[d]imidazol-5-yl)morpholine,
10) 4-chloro-2-(3-chloro-2,3'-bipyridin-6'-yl)-6-(trifluoromethyl)-1H-benzo[d]imidazole, and
11) 2-(3-chloro-2,3'-bipyridin-6'-yl)-4,6-bis(trifluoromethyl)-1H-benzo[d]imidazole.

Also, the compound represented by Chemical Formula 5 is any one selected from the group consisting of:
1) 4-(3-chloropyridin-2-yl)benzaldehyde,
2) 4-(3-chloropyridin-2-yl)-1-naphthaldehyde,
3) N-(3-fluoro-4'-formylbiphenyl-4-yl)methane sulfoneamide,
4) 4-(3-(trifluoromethyl)pyridin-2-yl)benzaldehyde,
5) 3-(trifluoromethyl)-2,3'-bipyridine-6'-carbaldehyde, and
6) 3-chloro-2,3'-bipyridine-6'-carbaldehyde.

Specifically, the present invention provides a method of preparing the compound represented by Chemical Formula 1, comprising the steps of 1-1(1), 1-1(2) and 2 in Scheme 1:

Step 1-1(1): reacting a compound represented by Chemical Formula 2 with a compound represented by Chemical Formula 3 in the presence of a palladium catalyst to prepare a compound represented by Chemical Formula 4;

Step 1-1(2): reacting the compound represented by Chemical Formula 4 with an oxidant to prepare a compound represented by Chemical Formula 5; and Step 2: reacting the compound represented by Chemical Formula 5 with a compound represented by Chemical Formula 6, to yield the compound of Chemical Formula 1.

In addition, the present invention provides a method of preparing the compound represented by Chemical Formula 1 including steps 1-2 and 2 in Scheme 1:

Step 1-2: reacting a compound represented by Chemical Formula 7 with a compound represented by Chemical Formula 3 in the presence of a palladium catalyst to prepare a compound represented by Chemical Formula 5; and Step 2: reacting the compound represented by Chemical Formula 5 with a compound represented by Chemical Formula 6, to yield the compound of Chemical Formula 1.

In Scheme 1, step 1-1(1) is a reaction where M is substituted into $R_1$ in the presence of a palladium catalyst. The palladium catalyst may be any one selected from the group consisting of $Pd(PPh_3)_4$, $Pd_2(dba)_3$, $PdCl_2(PPh_3)_2$ and $Pd(PtBu_3)_2$.

Also, the above reaction may be further performed in the presence of a base. The base may include an inorganic base or an organic base, and examples of the inorganic base may include calcium carbonate, sodium carbonate, potassium hydroxide, sodium hydroxide, cesium carbonate, potassium tert-butoxide (t-BuOK) and lithium hydroxide, and examples of the organic base may include triethylamine, tert-butylamine, and diisopropylethylamine. Taking into consideration the reaction yield, it is preferable to use $Pd(PPh_3)_4$ as the palladium catalyst and sodium carbonate as the base.

Further, the above reaction is preferably performed using a solvent such as ethanol, toluene, 1,2-dimethoxyethane, a mixture of water and ethanol, a mixture of water and toluene, or a mixture of water and 1,2-dimethoxyethane. In the mixture of water and ethanol, the mixture of water and toluene, or the mixture of water and 1,2-dimethoxyethane, the ratio of water and ethanol, water and toluene, and water and 1,2-dimethoxyethane may be 100:1~1:100.

Further, the reaction is preferably performed at 60~150° C., and more preferably at 80° C.~100° C.

In Scheme 1, step 1-1(2) is an oxidation reaction, using oxidants to oxidize into benzaldehyde. The oxidant may include selenium dioxide or ceric ammonium nitrate. It is preferable that the reaction may be performed using any one solvent selected from the group consisting of 1,4-dioxane, dimethylformamide, tetrahydrofuran, methanol and acetonitrile.

The reaction may be further performed in the presence of an acid in order to activate the oxidant. Examples of the acid include hydrochloric acid, nitric acid, sulfuric acid, phosphoric acid, acetic acid, p-toluene sulfonic acid (p-TSA), and camphorsulfonic acid (CSA). The acid may be added in an amount of 0.01~1.0 equivalents.

Also, the above reaction may be performed at 60° C.~150° C., and particularly at 80° C.~100° C.

In Scheme 1, step 1-2 is a reaction where M is substituted into $R_1$ in the presence of a palladium catalyst. The palladium catalyst may be any one selected from the group consisting of $Pd(PPh_3)_4$, $Pd_2(dba)_3$, $PdCl_2(PPh_3)_2$ and $Pd(P^tBu_3)_2$.

Also, the above reaction may be further performed in the presence of a base. The base may include an inorganic base or an organic base, and examples of the inorganic base include calcium carbonate, sodium carbonate, potassium hydroxide, sodium hydroxide, cesium carbonate, potassium tert-butoxide (t-BuOK) and lithium hydroxide, and examples of the organic base include triethylamine, tert-butylamine, and diisopropylethylamine. In consideration of the reaction yield, it is preferable to use $Pd(PPh_3)_4$ as the palladium catalyst and sodium carbonate as the base.

Also, the reaction is preferably performed using a solvent such as ethanol, toluene, 1,2-dimethoxyethane, a mixture of water and ethanol, a mixture of water and toluene, or a mixture of water and 1,2-dimethoxyethane. In the mixture of water and ethanol, the mixture of water and toluene, or the mixture of water and 1,2-dimethoxyethane, the ratio of water and ethanol, water and toluene, and water and 1,2-dimethoxyethane may be 100:1~1:100.

Also, the reaction is preferably performed at 60° C.~150° C., and more preferably at 80° C.~100° C.

By steps 1-1(1) and 1-1(2), or step 1-2, benzaldehyde which is an intermediate of the method according to the present invention may be prepared. As described below, in the case where the compound represented by Chemical Formula 1 is prepared using benzaldehyde, the need for expensive O-(7-azabenzotriazol-1-yl)-N,N,N,N-tetramethyluronium hexafluorophosphate which is conventionally used is obviated, unlike conventional methods, and as the preparation process may be simply conducted without distillation at high temperature, there may be fewer impurities thus increasing the purity and the yield.

In Scheme 1, step 2 is a reaction for preparing the compound represented by Chemical Formula 1 which is a target compound of the present invention using benzaldehyde as the intermediate.

In this reaction, the cyclization reaction may be performed using benzoquinone as an additive. In the case where benzoquinone is used as the additive, it is preferred that the reaction be carried out using any one solvent selected from the group consisting of 1,4-dioxane, acetonitrile, dimethylformamide, tetrahydrofuran and dimethylacetamide. In this case, the reaction may be performed at 60° C.~150° C., and preferably at 80° C.~100° C.

Alternatively, the cyclization reaction may be conducted without using benzoquinone as the additive. In this case, the reaction may be performed using any one solvent selected from the group consisting of xylene, toluene, nitrobenzene, and benzene. Furthermore, it is preferable the reaction be performed at 150° C.~250° C.

As shown in step 2 of Scheme 1, the method according to the present invention is advantageous because benzaldehyde is used as the intermediate, and thereby the need to use an expensive reagent is obviated and high yield and purity may result. A result of comparing the yield of the method according to the present invention with that of the conventional method showed that the yield was remarkably improved in the present invention. Therefore, compared to the conventional method, the method according to the present invention is very superior in terms of efficiency.

Advantageous Effects of Invention

According to the present invention, a novel method of preparing a benzoimidazole derivative is advantageous because a benzaldehyde derivative is obtained using an optimal solvent and via warming in the preparation process, so that the amount of impurities is minimized and simultaneously the reactivity is maximized, thus shortening the reaction time, resulting in high purity and high yield. Thus, benzoimidazole can be synthesized via a single reaction in lieu of a plurality of conventional reactions including condensation and cyclization. Furthermore, the method according to the present invention is simple by minimized impurities, does not require severe reaction conditions, and is very reproducible, thereby affording a highly pure benzoimidazole derivative at a high yield within a short period of time.

MODE FOR THE INVENTION

The following examples, which are set forth to illustrate but are not to be construed as limiting the present invention, may improve the understanding of the present invention.

Preparation Example

Preparation of trimethyl(p-tolyl)tin 100 g (0.585 mol) of 1-bromo-4-methylbenzene was dissolved in 500 mL of anhydrous ether in an argon atmosphere, and then cooled to −78° C. 252 mL (2.5M in hexane, 0.615 mol) of an n-butyl lithium solution was slowly added dropwise. The mixture was stirred for 15 minutes, and a solution of 122.6 g (0.615 mol) of trimethyltin chloride in 500 mL of ether was added. The mixture was stirred for 2 hours while the temperature was gradually increased to room temperature, followed by the addition of 700 mL of distilled water and then stirring. The organic layer was separated, treated with magnesium sulfate, filtered, and concentrated under reduced pressure, yielding trimethyl(p-tolyl)tin as represented below in a 77% yield.

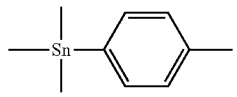

Example 1

Preparation of 6-tert-butyl-2-(4-(3-chloropyridin-2-yl)phenyl)-1H-benzo[d]imidazole 1) Example 1-1

Step 1-1(1): Preparation of 3-chloro-2-para-tolylpyridine 66.7 g (0.451 mol) of 2,3-dichloropyridine and 115 g (0.451 mol) of trimethyl(p-tolyl)tin were dissolved in 1 L of toluene, after which 52.1 g (0.045 mol) of Pd(PPh$_3$)$_4$ was added, and the mixture was heated to reflux for 6~7 hours. After completion of the reaction, the reaction solution was concentrated under reduced pressure and to the concentration residue was added 700 mL of distilled water, followed by stirring. The organic layer was separated, treated with magnesium sulfate, filtered, and concentrated under reduced pressure, yielding 3-chloro-2-para-tolylpyridine as represented below in a 82% yield.

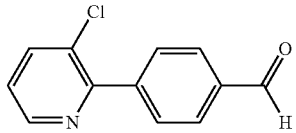

Step 1-1(2): Preparation of 4-(3-chloropyridin-2-yl)benzaldehyde

The title compound was prepared via the following two methods using different solvents and different oxidants.

① 100 g (0.49 mol) of 3-chloro-2-para-tolylpyridine was dissolved in 1 L of 1,4-dioxane in a reactor. 163.4 g (1.47 mol) of selenium dioxide was added, and the mixture was refluxed for 4~6 hours. The reaction solution was cooled to 25° C., and floating matter was filtered off with celite. A 10% sodium bicarbonate solution was added, and the mixture was extracted with ethyl acetate. The organic layer was dried with magnesium sulfate, and concentrated under reduced pressure, yielding 4-(3-chloropyridin-2-yl)benzaldehyde as represented below in a 85% yield.

② 100 g (0.49 mol) of 3-chloro-2-para-tolylpyridine was dissolved in 0.5 L of methanol in a reactor. A solution of 537 g (0.98 mol) of ceric ammonium nitrate in 1 L of methanol was added dropwise, and the mixture was refluxed for 4~6 hours. The reaction solution was cooled to 25° C. and concentrated under reduced pressure. A 10% sodium bicarbonate solution was added, and the mixture was extracted with ethyl acetate. The organic layer was dried with magnesium sulfate, and concentrated under reduced pressure, yielding 4-(3-chloropyridin-2-yl)benzaldehyde as represented below in a 60% yield.

$^1$H NMR (CDCl$_3$) δ: 10.10 (s, 1H), 8.63 (dd, 1H), 8.00 (d, 2H), 7.91 (d, 2H), 7.85 (dd, 1H), 7.30 (dd, 1H)

Step 2: Preparation of 6-tert-butyl-2-(4-(3-chloropyridin-2-yl)phenyl)-1H-benzo[d]imdiazole The title compound was prepared via the following three methods using different solvents in the presence or absence of benzoquinone.

① 84.4 g (0.39 mol) of 4-(3-chloropyridin-2-yl)benzaldehyde and 840 mL of nitrobenzene were sequentially placed in a reactor. 63.7 g (0.39 mol) of 4-tert-butylbenzene-1,2-diamine was added. The mixture was heated to reflux for 2 hours, cooled to room temperature and concentrated under reduced pressure. To the residue was added 340 mL of acetonitrile, and the mixture was heated to reflux so as to be completely dissolved, slowly cooled to 0~5° C., stirred at the same temperature for 2 hours, filtered, and dried in a vacuum at 50° C., yielding the following compound in a 88.7% yield.

② 84.4 g (0.39 mol) of 4-(3-chloropyridin-2-yl)benzaldehyde and 840 mL of acetonitrile were sequentially placed in a reactor. 63.7 g (0.39 mol) of 4-tert-butylbenzene-1,2-diamine and 42.1 g (0.39 mol) of 1,4-benzoquinone were added. The mixture was heated to reflux for 2 hours, cooled to room temperature and concentrated under reduced pressure. 340 mL of acetonitrile was added to the residue, and the mixture was heated to reflux so as to be completely dissolved, slowly cooled to 0~5° C., stirred at the same temperature for 2 hours, filtered and dried in a vacuum at 50° C., yielding the following compound in a 91% yield.

③ The following compound was obtained in a 90% yield in the same manner as in ②, with the exception that 1,4-dioxane was used as the solvent instead of acetonitrile.

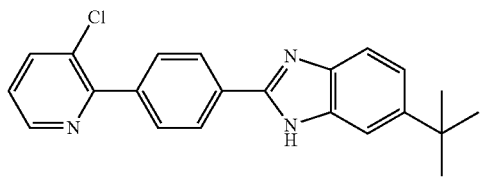 [SMILES: CC(C)(C)c1ccc2nc(-c3ccc(-c4ncccc4Cl)cc3)[nH]c2c1]

$^1$H NMR (CDCl$_3$) δ: 8.57 (d, 1H), 8.03 (d, 2H), 7.77 (d, 1H), 7.62 (d, 2H), 7.51 (s, 1H), 7.46 (d, 1H), 7.25-7.21 (m, 2H), 1.27 (s, 9H)

2) Example 1-2

Step 1-1(1): Preparation of 3-chloro-2-para-tolylpyridine

The title compound was prepared via the following two methods using different solvents.

① 100 g (0.676 mol) of 2,3-dichloropyridine, 91.87 g (0.676 mol) of p-tolylboronic acid, and 86 g (0.811 mol) of sodium carbonate were dissolved in 500 mL of 1,2-dimethoxyethane and 500 mL of distilled water, after which 78 g (0.0676 mol) of Pd(PPh$_3$)$_4$ was added. The mixture was heated to reflux for 18 hours so that it was allowed to react. After completion of the reaction, the reaction solution was concentrated under reduced pressure to remove 1,2-dimethoxyethane, and then extracted with ethyl acetate. The extract was treated with magnesium sulfate, filtered, and concentrated under reduced pressure, yielding 3-chloro-2-para-tolylpyridine as represented below in a 84% yield.

② 100 g (0.676 mol) of 2,3-dichloropyridine was dissolved in 500 mL of ethanol, and 91.87 g (0.676 mol) of p-tolylboronic acid and 78 g (0.0676 mol) of Pd(PPh$_3$)$_4$ were sequentially added. A solution of 86 g (0.811 mol) of sodium carbonate in 500 mL of distilled water was placed in the reactor, and the mixture was heated to reflux for 4~6 hours so as to allow it to react. After completion of the reaction, the reaction solution was concentrated under reduced pressure to remove ethanol, and then extracted with ethyl acetate. The extract was treated with magnesium sulfate, filtered, and concentrated under reduced pressure, yielding 3-chloro-2-para-tolylpyridine as represented below in a 87% yield.

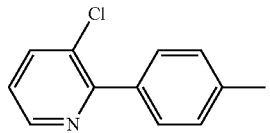

Step 1-1 (2): Preparation of 4-(3-chloropyridin-2-yl)benzaldehyde 100 g (0.49 mol) of 3-chloro-2-para-tolylpyridine was dissolved in 1 L of 1,4-dioxane in a reactor. 163.4 g (1.47 mol) of selenium dioxide was added, and the mixture was refluxed for 4~6 hours. The reaction solution was cooled to 25° C., and floating matter was filtered off with celite. A 10% sodium bicarbonate solution was added, and the mixture was extracted with ethyl acetate. The organic layer was dried with magnesium sulfate and concentrated under reduced pressure, yielding 4-(3-chloropyridin-2-yl)benzaldehyde as represented below in a 85% yield.

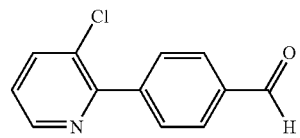 [SMILES: O=Cc1ccc(-c2ncccc2Cl)cc1]

Step 2: Preparation of 6-tert-butyl-2-(4-(3-chloropyridin-2-yl)phenyl)-1H-benzo[d]imidazole 6-tert-butyl-2-(4-(3-chloropyridin-2-yl)phenyl)-1H-benzo[d]imidazole as represented below was obtained in a 88~91% yield in the same manner as in step 2 of Example 1-1.

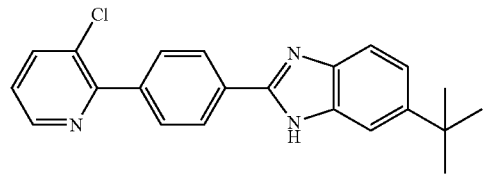 [SMILES: CC(C)(C)c1ccc2nc(-c3ccc(-c4ncccc4Cl)cc3)[nH]c2c1]

3) Example 1-3

Step 1-2: Preparation of 4-(3-chloropyridin-2-yl)benazaldehyde

The title compound was prepared via the following two methods using different solvents.

① 100 g (0.676 mol) of 2,3-dichloropyridine, 101.4 g (0.676 mol) of (4-formylphenyl)boronic acid and 86 g (0.811 mol) of sodium carbonate were dissolved in 500 mL of 1,2-dimethoxyethane and 500 mL of distilled water, and 78 g (0.0676 mol) of Pd(PPh3)4 was added. The mixture was heated to reflux for 18 hours so that it was allowed to react. After completion of the reaction, the reaction solution was concentrated under reduced pressure to remove 1,2-dimethoxyethane, and then extracted with ethyl acetate. The extract was treated with magnesium sulfate, filtered and concentrated under reduced pressure, yielding 4-(3-chloropyridin-2-yl)benzaldehyde as represented below in a 81% yield.

② 100 g (0.676 mol) of 2,3-dichloropyridine was dissolved in 500 mL of ethanol, and 101.4 g (0.676 mol) of (4-formylphenyl)boronic acid and 78 g (0.0676 mol) of Pd(PPh$_3$)$_4$ were sequentially added. A solution of 86 g (0.811 mol) of sodium carbonate in 500 mL of distilled water was placed in the reactor, and the mixture was heated to reflux for 4~6 hours so as to allow it to react. After completion of the reaction, the reaction solution was concentrated under reduced pressure to remove ethanol, and extracted with ethyl acetate. The extract was treated with magnesium sulfate, filtered and concentrated under reduced pressure, yielding 4-(3-chloropyridin-2-yl)benzaldehyde as represented below in a 83% yield.

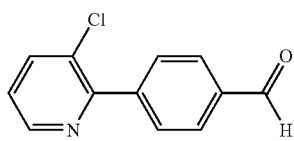

Step 2: Preparation of 6-tert-butyl-2-(4-(3-chloropyridin-2-yl)phenyl)-1H-benzo[d]imidazole 6-tert-butyl-2-(4-(3-chloropyridin-2-yl)phenyl)-1H-benzo[d]imidazole as represented below was obtained in a 88~91% yield in the same manner as in step 2 of Example 1-1.

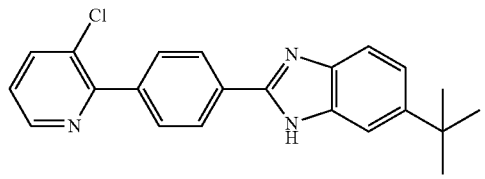 [SMILES: CC(C)(C)c1ccc2nc(-c3ccc(-c4ncccc4Cl)cc3)[nH]c2c1]

Example 2

Preparation of 6-tert-butyl-2-(4-(3-chloropyridin-2-yl)naphthalen-1-yl)-1H-benzo[d]imidazole

Step 1: Preparation of 4-(3-chloropyridin-2-yl)-1-naphthaldehyde

The title compound was prepared via the following two methods.

① 4-(3-chloropyridin-2-yl)-1-naphthaldehyde as represented below was obtained in a 81% yield in the same manner as in step 1-1(1) and step 1-1(2) of Example 1-2, with the exception that 4-methylnaphthalen-1-yl boronic acid was used instead of p-tolylboronic acid.

② 4-(3-chloropyridin-2-yl)-1-naphthaldehyde as represented below was obtained in a 80% yield in the same manner as in step 1-2 of Example 1-3, with the exception that 4-formylnaphthalen-1-yl boronic acid was used instead of (4-formylphenyl)boronic acid.

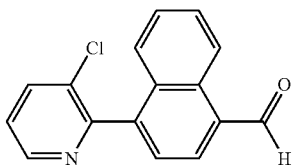

$^1$H NMR (CDCl$_3$) δ: 10.11 (s, 1H), 8.72 (d, 1H), 8.62 (d, 1H), 8.10 (d, 1H), 7.98 (d, 1H), 7.80-7.74 (m, 5H)

Step 2: Preparation of 6-tert-butyl-2-(4-(3-chloropyridin-2-yl)naphthalen-1-yl)-1H-benzo[d]imidazole 6-tert-butyl-2-(4-(3-chloropyridin-2-yl)naphthalen-1-yl)-1H-benzo[d]imidazole as represented below was obtained in a 97% yield in the same manner as in step 2 of Example 1-1.

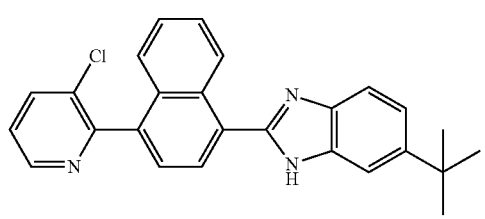 [SMILES: CC(C)(C)c1ccc2nc(-c3ccc(-c4ncccc4Cl)c4ccccc34)[nH]c2c1]

$^1$H NMR (CD$_3$OD) δ: 8.66 (d, 1H), 8.65 (d, 1H), 8.13 (d, 1H), 7.98 (d, 1H), 7.71 (s, 1H), 7.64-7.58 (m, 5H), 7.47-7.44 (m, 2H), 1.44 (s, 9H)

Example 3

Preparation of N-(4'-(4,6-bis(trifluoromethyl)-1H-benzo[d]imidazol-2-yl)-3-fluorobiphenyl-4-yl)methanesulfonamide

Step 1: Preparation of N-(3-fluoro-4'-formylbiphenyl-4-yl)methanesulfoneamide The title compound was prepared via the following two methods.

① N-(3-fluoro-4'-formylbiphenyl-4-yl)methane sulfoneamide as represented below was obtained in a 80% yield in the same manner as in step 1-1(1) and step 1-1(2) of Example 1-2, with the exception that N-(4-chloro-2-fluorophenyl)methanesulfoneamide was used instead of 2,3-dichloropyridine.

② N-(3-fluoro-4'-formylbiphenyl-4-yl)methane sulfoneamide as represented below was obtained in a 79% yield in the same manner as in step 1-2 of Example 1-3, with the exception that N-(4-chloro-2-fluorophenyl)methanesulfoneamide was used instead of 2,3-dichloropyridine.

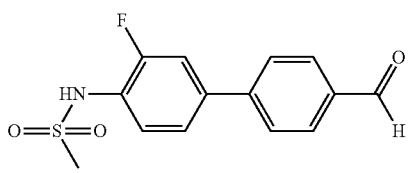 [SMILES: CS(=O)(=O)Nc1ccc(-c2ccc(C=O)cc2)cc1F]

$^1$H NMR (CDCl$_3$) δ: 10.07 (s, 1H), 7.97 (d, 2H), 7.71 (d, 3H), 7.67-7.42 (m, 2H), 6.59 (br, 1H), 3.09 (s, 3H)

Step 2: Preparation of N-(4'-(4,6-bis(trifluoromethyl)-1H-benzo[d]imidazol-2-yl)-3-fluorobiphenyl-4-yl)methanesulfoneamine N-(4'-(4,6-bis(trifluoromethyl)-1H-benzo[d]imidazol-2-yl)-3-fluorobiphenyl-4-yl)methanesulfoneamide as represented below was obtained in a 76% yield in the same manner as in step 2 of Example 1-1, with the exception that 3,5-bis(trifluoromethyl)benzene-1,2-diamine was used instead of 4-tert-butylbenzene-1,2-diamine.

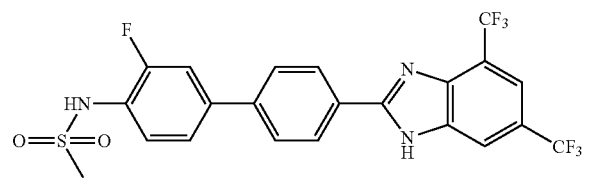 [SMILES: CS(=O)(=O)Nc1ccc(-c2ccc(-c3nc4c(C(F)(F)F)cc(C(F)(F)F)cc4[nH]3)cc2)cc1F]

$^1$H NMR (CD$_3$OD) δ: 8.13 (d, 2H), 7.83 (d, 2H), 7.72 (s, 1H), 7.68-7.62 (m, 2H), 7.59-7.55 (m, 2H), 3.07 (s, 3H)

Example 4

Preparation of 4-bromo-6-(trifluoromethyl)-2-(4-(3-(trifluoromethyppyridin-2-yl)phenyl)-1H-benzo[d]imidazole

Step 1: Preparation of 4-(3-(trifluoromethyl)pyridin-2-yl)benzaldehyde

The title compound was prepared via the following two methods.

① 4-(3-(trifluoromethyl)pyridin-2-yl)benzaldehyde as represented below was obtained in a 85% yield in the same manner as in step 1-1(1) and step 1-1(2) of Example 1-2, with the exception that 2-chloro-3-(trifluoromethyl)pyridine was used instead of 2,3-dichloropyridine.

② 4-(3-(trifluoromethyl)pyridin-2-yl)benzaldehyde as represented below was obtained in a 82% yield in the same manner as in step 1-2 of Example 1-3, with the exception that 2-chloro-3-(trifluoromethyl)pyridine was used instead of 2,3-dichloropyridine.

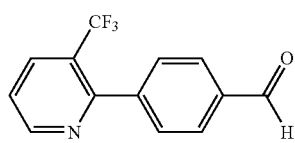

$^1$H NMR (CDCl$_3$) δ: 10.09 (s, 1H), 8.87 (d, 1H), 8.11 (d, 1H), 7.97 (d, 2H), 7.67 (d, 2H), 7.49 (dd, 1H)

Step 2: Preparation of 4-bromo-6-(trifluoromethyl)-2-(4-(3-(trifluoromethyl)pyridin-2-yl)phenyl)-1H-benzo[d]imidazole 4-bromo-6-(trifluoromethyl)-2-(4-(3-(trifluoromethyl)pyridin-2-yl)phenyl)-1H-benzo[d]imidazole as represented below was obtained in a 84% yield in the same manner as in step 2 of Example 1-1, with the exception that 3-bromo-5-(trifluoromethyl)benzene-1,2-diamine was used instead of 4-tert-butylbenzene-1,2-diamine.

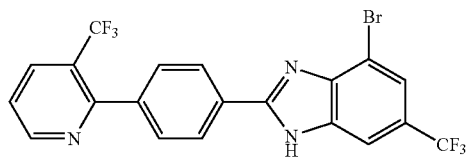 [SMILES: FC(F)(F)c1cc(Br)c2nc(-c3ccc(-c4ncccc4C(F)(F)F)cc3)[nH]c2c1]

$^1$H NMR (CDCl$_3$) δ: 8.95 (d, 1H), 8.19-8.12 (m, 3H), 7.96 (s, 1H), 7.73 (s, 1H), 7.65 (d, 2H), 7.57-7.53 (m, 1H)

Example 5

Preparation of 6-bromo-2-(4-(3-(trifluoromethyppyridin-2-yl)phenyl)-1H-imidazo[4,5-b]pyridine

Step 1: Preparation of 4-(3-(trifluoromethyl)pyridin-2-yl)benzaldehyde 4-(3-(trifluoromethyl)pyridin-2-yl)benzaldehyde was obtained in a 85% yield in the same manner as in step 1 of Example 4.

Step 2: Preparation of 6-bromo-2-(4-(3-(trifluoromethyl)pyridin-2-yl)phenyl)-1H-imidazo[4,5-b]pyridine 6-bromo-2-(4-(3-(trifluoromethyl)pyridin-2-yl)phenyl)-1H-imidazo[4,5-b]pyridine as represented below was obtained in a 75% yield in the same manner as in step 2 of Example 1-1, with the exception that 5-bromopyridine-2,3-diamine was used instead of 4-tert-butylbenzene-1,2-diamine.

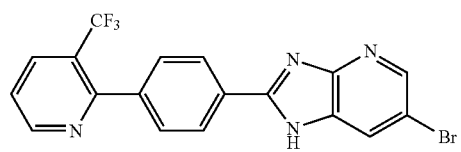

$^1$H NMR (CDCl$_3$) δ: 8.93 (d, 1H), 8.45 (s, 1H), 8.29 (d, 2H), 8.26 (s, 1H), 8.15 (dd, 1H), 7.72 (d, 2H), 7.52 (dd, 1H)

Example 6

Preparation of 6-(trifluoromethyl)-2-(3-(trifluoromethyl)-2,3'-bipyridin-6'-yl)-1H-benzo[d]imidazole

Step 1: Preparation of 3-(trifluoromethyl)-2,3'-bipyridine-6'-carbaldehyde

The title compound was prepared via the following three methods.

① 3-(trifluoromethyl)-2,3'-bipyridine-6'-carbaldehyde as represented below was obtained in a 83% yield in the same manner as in step 1-1(1) and step 1-1(2) of Example 1-1, with the exception that 2-methyl-5-(trimethylstenyl)pyridine and 2-chloro-3-(trifluoromethyl)pyridine were used instead of trimethyl(p-tolyl)tin and 2,3-dichloropyridine, respectively.

② 3-(trifluoromethyl)-2,3'-bipyridine-6'-carbaldehyde as represented below was obtained in a 84% yield in the same manner as in step 1-1(1) and step 1-1(2) of Example 1-2, with the exception that 2-chloro-3-(trifluoromethyl)pyridine and 6-methylpyridin-3-yl boronic acid were used instead of 2,3-dichloropyridine and p-tolylboronic acid, respectively.

③ 3-(trifluoromethyl)-2,3'-bipyridine-6'-carbaldehyde as represented below was obtained in a 81% yield in the same manner as in step 1-2 of Example 1-3, with the exception that 2-chloro-3-(trifluoromethyl)pyridine and 6-formylpyridin-3-yl boronic acid were used instead of 2,3-dichloropyridine and (4-formylphenyl)boronic acid, respectively, and 0.2 equivalents of nitric acid (60~62%) was added.

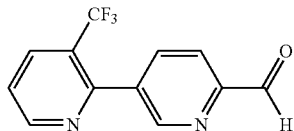

¹H NMR (CDCl₃) δ: 10.16 (s, 1H), 8.92 (d, 2H), 8.16 (d, 1H), 8.09-8.04 (m, 2H), 7.57-7.53 (m, 2H)

Step 2: Preparation of 6-(trifluoromethyl)-2-(3-(trifluoromethyl)-2,3'-bipyridin-6'-yl)-1H-benzo[d]imidazole 6-(trifluoromethyl)-2-(3-(trifluoromethyl)-2,3'-bipyridin-6'-yl)-1H-benzo[d]imidazole was obtained in a 95% yield in the same manner as in step 2 of Example 1-1, with the exception that 4-(trifluoromethyl)benzene-1,2-diamine was used instead of 4-tert-butylbenzene-1,2-diamine.

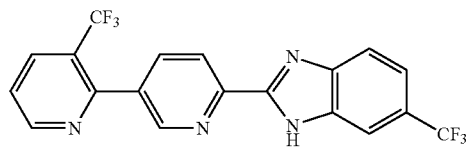 [SMILES: FC(F)(F)c1ccc2nc(-c3ccc(-c4ncccc4C(F)(F)F)cn3)[nH]c2c1]

¹H NMR (CDCl₃) δ: 8.94 (d, 1H), 8.84 (s, 1H), 8.61 (d, 1H), 8.19 (d, 1H), 8.11 (d, 1H), 8.10 (s, 1H), 8.08 (d, 1H), 7.61-7.54 (m, 2H)

Example 7

Preparation of 6-bromo-2-(3-(trifluoromethyl)-2,3'-bipyridin-6'-yl)-1H-benzo[d]imidazole Step 1: Preparation of 3-(trifluoromethyl)-2,3'-bipyridine-6'-carbaldehyde 3-(trifluoromethyl)-2,3'-bipyridine-6'-carbaldehyde was obtained in a 84% yield in the same manner as in step 1 of Example 6.

Step 2: Preparation of 6-bromo-2-(3-(trifluoromethyl)-2,3'-bipyridin-6'-yl)-1H-benzo[d]imidazole 6-bromo-2-(3-(trifluoromethyl)-2,3'-bipyridin-6'-yl)-1H-benzo[d]imidazole as represented below was obtained in a 87% yield in the same manner as in step 2 of Example 1-1, with the exception that 4-bromobenzene-1,2-diamine was used instead of 4-tert-butylbenzene-1,2-diamine.

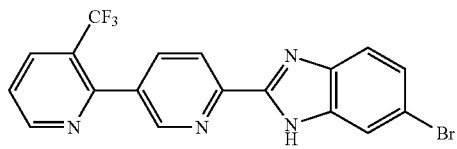 [SMILES: FC(F)(F)c1cccnc1-c1ccc(-c2nc3ccc(Br)cc3[nH]2)nc1]

¹H NMR (CD₃OD) δ: 8.90 (dd, 1H), 8.81 (d, 1H), 8.35 (dd, 1H), 8.29 (dd, 1H), 8.07 (dd, 1H), 7.80-7.70 (br, 1H), 7.67 (dd, 1H), 7.65-7.55 (br, 1H), 7.41 (dd, 1H)

Example 8

Preparation of 6-bromo-2-(3-(trifluoromethyl)-2,3'-bipyridin-6'-yl)-1H-imidazo[4,5-b]pyridine Step 1: Preparation of 3-(trifluoromethyl)-2,3'-bipyridine-6'-carbaldehyde 3-(trifluoromethyl)-2,3'-bipyridine-6'-carbaldehyde was obtained in a 84% yield in the same manner as in step 1 of Example 6.

Step 2: Preparation of 6-bromo-2-(3-(trifluoromethyl)-2,3'-bipyridin-6'-yl)-1H-imidazo[4,5-b]pyridine 6-bromo-2-(3-(trifluoromethyl)-2,3'-bipyridin-6'-yl)-1H-imidazo[4,5-b]pyridine as represented below was obtained in a 70% yield in the same manner as in step 2 of Example 1-1, with the exception that 5-bromopyridine-2,3-diamine was used instead of 4-tert-butylbenzene-1,2-diamine.

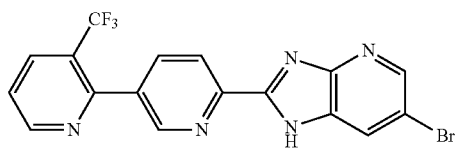 [SMILES: FC(F)(F)c1cccnc1-c1ccc(-c2nc3ncc(Br)cc3[nH]2)nc1]

¹H NMR (CDCl₃) δ: 9.79 (s, 1H), 8.91 (dd, 1H), 8.74 (d, 1H), 8.35 (dd, 1H), 8.15 (dd, 1H), 8.10 (dd, 1H), 8.03 (d, 1H), 7.54 (dd, 1H)

Example 9

Preparation of 4-(2-(3-(trifluoromethyl)-2,3'-bipyridin-6'-yl)-3H-benzo[d]imidazol-5-yl)morpholine Step 1: Preparation of 3-(trifluoromethyl)-2,3'-bipyridine-6'-carbaldehyde 3-(trifluoromethyl)-2,3'-bipyridin-6'-carbaldehyde was obtained in a 84% yield in the same manner as in step 1 of Example 6.

Step 2: Preparation of 4-(2-(3-(trifluoromethyl)-2,3'-bipyridin-6'-yl)-1H-benzo[d]imidazol-6-yl)morpholine 4-(2-(3-(trifluoromethyl)-2,3'-bipyridin-6'-yl)-1H-benzo[d]imidazol-6-yl)morpholine was obtained in a 79% yield in the same manner as in step 2 of Example 1-1, with the exception that 4-morpholinebenzene-1,2-diamine was used instead of 4-tert-butylbenzene-1,2-diamine.

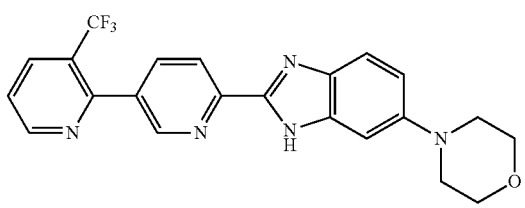 [SMILES: FC(F)(F)c1cccnc1-c1ccc(-c2nc3ccc(N4CCOCC4)cc3[nH]2)nc1]

¹H NMR (CD₃OD) δ: 8.90 (d, 1H), 8.80 (s, 1H), 8.33 (dd, 1H), 8.27 (dd, 1H), 8.07 (dd, 1H), 7.75-7.81 (br, 1H), 7.66 (dd, 1H), 7.65-7.55 (br, 1H), 7.41 (dd, 1H), 3.88-3.92 (m, 4H), 3.32-3.29 (m, 4H)

Example 10

Preparation of 4-chloro-2-(3-chloro-2,3'-bipyridin-6'-yl)-6-(trifluoromethyl)-1H-benzo[d]imidazole Step 1: Preparation of 3-chloro-2,3'-bipyridine-6'-carbaldehyde The title compound was prepared via the following two methods.

① 3-chloro-2,3'-bipyridine-6'-carbaldehyde as represented below was obtained in a 82% yield in the same manner as in step 1-1(1) and step 1-1(2) of Example 1-2, with the exception that 6-methylpyridin-3-yl boronic acid was used instead of p-tolylboronic acid.

② 3-chloro-2,3'-bipyridine-6'-carbaldehyde as represented below was obtained in a 81% yield in the same manner as in step 1-2 of Example 1-3, with the exception that 6-formulpyridin-3-yl boronic acid was used instead of (4-formylphenyl)boronic acid.

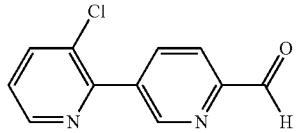 [SMILES: O=Cc1ccc(-c2ncccc2Cl)cn1]

¹H NMR (CDCl₃) δ: 10.16 (s, 1H), 9.18 (d, 1H), 8.67 (dd, 1H), 8.28 (dd, 1H), 8.07 (d, 1H), 7.87 (dd, 1H), 7.37-7.32 (m, 1H)

Step 2: Preparation of 4-chloro-2-(3-chloro-2,3'-bipyridin-6'-yl)-6-(trifluoromethyl)-1H-benzo[d]imidazole 4-chloro-2-(3-chloro-2,3'-bipyridin-6'-yl)-6-(trifluoromethyl)-1H-benzo[d]imidazole as represented below was obtained in a 83% yield in the same manner as in step 2 of Example 1-1, with the exception that 3-chloro-5-(trifluoromethyl)benzene-1,2-diamine was used instead of 4-tert-butylbenzene-1,2-diamine.

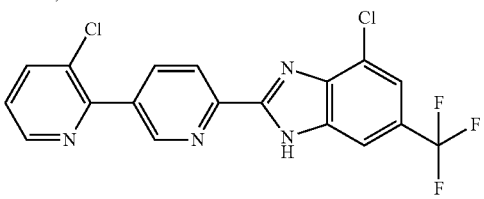

¹H NMR (CDCl₃) δ: 9.10 (d, 1H), 8.68 (d, 1H), 8.52 (d, 1H), 8.38-8.31 (m, 1H), 8.05 (s, 1H), 7.88 (d, 1H), 7.59 (s, 1H), 7.36-7.29 (m, 1H)

Example 11

Preparation of 2-(3-chloro-2,3'-bipyridin-6'-yl)-4,6-bis(trifluoromethyl)-1H-benzo[d]imidazole Step 1: Preparation of 3-chloro-2,3'-bipyridine-6'-carbaldehyde 3-chloro-2,3'-bipyridine-6'-carbaldehyde was obtained in a 82% yield in the same manner as in step 1 of Example 10.

Step 2: Preparation of 2-(3-chloro-2,3'-bipyridin-6'-yl)-4,6-bis(trifluoromethyl)-1H-benzo[d]imidazole 2-(3-chloro-2,3'-bipyridin-6'-yl)-4,6-bis(trifluoromethyl)-1H-benzo[d]imidazole as represented below was obtained in a 80% yield in the same manner as in step 2 of Example 1-1, with the exception that 3,5-bis(trifluoromethyl)benzene-1,2-diamine was used instead of 4-tert-butylbenzene-1,2-diamine.

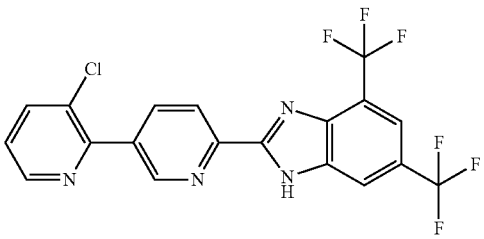 [SMILES: FC(F)(F)c1cc(C(F)(F)F)c2nc(-c3ccc(-c4ncccc4Cl)cn3)[nH]c2c1]

¹H NMR (CDCl₃) δ: 9.08 (s, 1H), 8.65 (d, 1H), 8.51 (d, 1H), 8.33-8.28 (m, 2H), 7.85 (d, 1H), 7.80 (s, 1H), 7.34-7.31 (m, 1H)

The yields of the above examples are shown in Table 1 below, and compared with Korean Patent Publication No. 10-2007-0113207 that discloses a conventional method of preparing a benzoimidazole derivative.

TABLE 1

| Ex.No. | Chemical Formula | Step [1-1(1)] Step [1-2] | Step [1-1(2)] | Step [2] | Total Yield | Korean Patent Publication No.10-2007-0113207 |
|---|---|---|---|---|---|---|
| 1-1 | | 82% | 85%, 60% | 88.7%, 91%, 90% | 63.4% | 66.0% |
| 1-2 | | 84%, 87% | 85% | 88~91% | 67.3% | |
| 1-3 | | 81%, 83% | | 88~91% | 75.5% | |

TABLE 1-continued

| Ex.No. | Chemical Formula | Step [1-1(1)] Step [1-2] | Step [1-1(2)] | Step [2] | Total Yield | Korean Patent Publication No.10-2007-0113207 |
|---|---|---|---|---|---|---|
| 2 | | 83~87% 80% | 81% | 97% | 68.3% 77.6% | 33.4% |
| 3 | | 83~87% 79% | 80% | 76% | 52.9% 60.0% | 36.0% |
| 4 | | 83~87% 82% | 85% | 84% | 62.1% 68.9% | 57.0% |
| 5 | | 83~87% 82% | 85% | 75% | 55.5% 61.5% | 45.7% |
| 6 | | 83~87% 81% | 83%, 84% | 95% | 69.4% 77.0% | 57.8% |
| 7 | | 83~87% 81% | 83%, 84% | 87% | 63.6% 70.5% | 40.6% |
| 8 | | 83~87% 81% | 83%, 84% | 70% | 51.2% 56.7% | 32.0% |
| 9 | | 83~87% 81% | 83%, 84% | 79% | 57.7% 64.0% | 46.9% |

TABLE 1-continued

| Ex.No. | Chemical Formula | Step [1-1(1)] Step [1-2] | Step [1-1(2)] | Step [2] | Total Yield | Korean Patent Publication No.10-2007-0113207 |
|---|---|---|---|---|---|---|
| 10 | | 83~87% 81% | 82% | 83% | 59.2% 67.2% | 42.5% |
| 11 | | 83~87% 81% | 82% | 80% | 57.0% 64.8% | 38.0% |

As is apparent from Table 1, the method according to the present invention can be improved in terms of yield, compared to the conventional method of preparing a benzoimidazole derivative, and thereby the benzoimidazole derivatives can be prepared using a simple process without the use of expensive reagents.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A method of preparing a benzimidazole compound, comprising the steps of:
   1) reacting a compound represented by Chemical Formula 2 below with a compound represented by Chemical Formula 3 below in the presence of a palladium catalyst to prepare a compound represented by Chemical Formula 4 below;
   2) reacting the compound represented by Chemical Formula 4 with an oxidant to prepare an intermediate compound wherein said intermediate compound is selected from the group consisting of:
   4-(3-chloropyridin-2-yl)-1-naphthaldehyde,
   N-(3-fluoro-4'-formylbiphenyl-4-yl)methane sulfoneamide,
   4-(3-(trifluoromethyl)pyridin-2-yl)benzaldehyde,
   3-(trifluoromethyl)-2,3'-bipyridine-6'-carbaldehyde, and
   3-chloro-2,3'-bipyridine-6'-carbaldehyde; and
   3) reacting the intermediate compound with a compound represented by the Chemical Formula 6 below, to yield the benzimidazole compound, wherein step 3) is performed using 1,4-benzoquinone as an additive and 1,4-dioxane or acetonitrile as a solvent,
   wherein said benzimidazole compound is selected from the group consisting of: 6-tert-butyl-2-(4-(3-chloropyridin-2-yl)naphthalen-1-yl)-1H-benzo[d]imidazole, N-(4'-(4,6-bis(trifluoromethyl)-1H-benzo[d]imidazol-2-yl)-3-fluorobiphenyl-4-yl)methanesulfoneamide,
   6-bromo-2-(3-(trifluoromethyl)-2,3'-bipyridin-6'-yl)-1H-benzo[d]imidazole, 6-bromo-2-(3-(trifluoromethyl)-2,3'-bipyridin-6'-yl)-1H-imidazo[4,5-b]pyridine, 4-chloro-2-(3-chloro-2,3'-bipyridin-6'-yl)-6-(trifluoromethyl)-1H-benzo[d]imidazole, and 2-(3-chloro-2,3'-bipyridin-6'-yl)-4,6-bis(trifluoromethyl)-1H-benzo[d]imidazole,

[Chemical Formula 2]

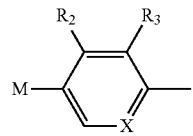

[Chemical Formula 3]

[Chemical Formula 4]

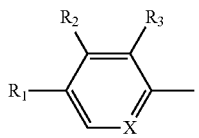

[Chemical Formula 6]

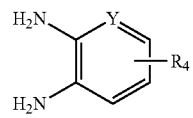

wherein M is B(OH)$_2$, B(i-Pr)$_2$, Sn(CH$_3$)$_3$, or SnBu$_3$,

X is CH or N,

Y is CR$_5$ or N,

R₁ is

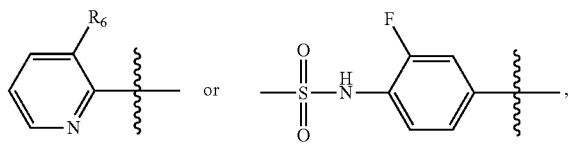

R₂ and R₃ each are hydrogen or R₂ and R₃ together form a benzene ring,
R₄ is Br, tert-butyl, or trifluoromethyl,
R₅ is hydrogen, Cl, or trifluoromethyl, and
R₆ is hydrogen, Cl, or trifluoromethyl.

2. A method of preparing a benzimidazole compound, comprising the steps of:
1) reacting a compound represented by Chemical Formula 7 below with a compound represented by Chemical Formula 3 below in the presence of a palladium catalyst to prepare an intermediate compound, wherein said intermediate compound is selected from the group consisting of:
4-(3-chloropyridin-2-yl)-1-naphthaldehyde,
N-(3-fluoro-4'-formylbiphenyl-4-yl)methane sulfoneamide,
4-(3-(trifluoromethyl)pyridin-2-yl)benzaldehyde,
3-(trifluoromethyl)-2,3'-bipyridine-6'-carbaldehyde, and
3-chloro-2,3'-bipyridine-6'-carbaldehyde; and
2) reacting the intermediate compound with a compound represented by Chemical Formula 6 below, to yield the benzimidazole compound, wherein the step 3) is performed using 1,4-benzoquinone as an additive and 1,4-dioxane or acetonitrile as a solvent,
wherein said benzimidazole compound is selected from the group consisting of:
6-tert-butyl-2-(4-(3-chloropyridin-2-yl)naphthalen-1-yl)-1H-benzo[d]imidazole,
N-(4'-(4,6-bis(trifluoromethyl)-1H-benzo[d]imidazol-2-yl)-3-fluorobiphenyl-4-yl)methanesulfoneamide,
4-bromo-6-(trifluoromethyl)-2-(4-(3-(trifluoromethyl)pyridin-2-yl)phenyl)-1H-benzo[d]imidazole,
6-bromo-2-(4-(3-(trifluoromethyl)pyridin-2-yl)phenyl)-1H-imidazo[4,5-b]pyridine,
6-(trifluoromethyl)-2-(3-(trifluoromethyl)-2,3'-bipyridin-6'-yl)-1H-benzo[d]imidazole,
6-bromo-2-(3-(trifluoromethyl)-2,3'-bipyridin-6'-yl)-1H-benzo[d]imidazole,
6-bromo-2-(3-(trifluoromethyl)-2,3'-bipyridin-6'-yl)-1H-imidazo[4,5-b]pyridine,
4-(2-(3-(trifluoromethyl)-2,3'-bipyridin-6'-yl)-3H-benzo[d]imidazol-5-yl)morpholine,
4-chloro-2-(3-chloro-2,3'-bipyridin-6'-yl)-6-(trifluoromethyl)-1H-benzo[d]imidazole, and
2-(3-chloro-2,3'-bipyridin-6'-yl)-4,6-bis(trifluoromethyl)-1H-benzo[d]imidazole;

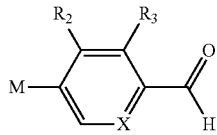 [Chemical Formula 3]

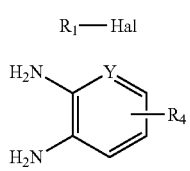 [Chemical Formula 6]

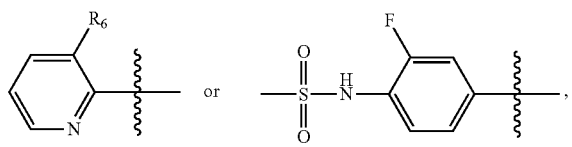 [Chemical Formula 7]

wherein M is B(OH)₂, B(i-Pr)₂, Sn(CH₃)₃, or SnBu₃,
X is CH or N,
Y is CR₅ or N,
R₁ is

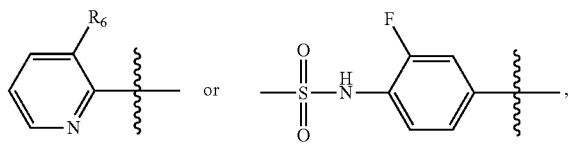

R₂ and R₃ each are hydrogen or R₂ and R₃ together form a benzene ring,
R₄ is Br, tert-butyl, trifluoromethyl, or morpholino,
R₅ is hydrogen, Cl, Br, or trifluoromethyl, and
R₆ is hydrogen, Cl, or trifluoromethyl.

3. The method of claim 1 or 2, wherein said palladium catalyst is any one selected from the group consisting of Pd(PPh₃)₄, Pd₂(dba)₃, PdCl₂(PPh₃)₂ and Pd(PᵗBu₃)₂.

4. The method of claim 1 or 2, wherein the step 1) of claim 1 or the step 1) of claim 2 is further performed in the presence of a base.

5. The method of claim 4, wherein the base is an inorganic base or an organic base.

6. The method of claim 5, wherein the inorganic base is any one selected from the group consisting of calcium carbonate, sodium carbonate, potassium hydroxide, sodium hydroxide, cesium carbonate, potassium tert-butoxide (t-BuOK) and lithium hydroxide.

7. The method of claim 5, wherein the organic base is any one selected from the group consisting of triethylamine, tert-butylamine, and diisopropylethylamine.

8. The method of claim 1 or 2, wherein the step 1) of claim 1 or the step 1) of claim 2 is performed using any one solvent selected from the group consisting of ethanol, toluene, 1,2-dimethoxyehtane, a mixture of water and ethanol, a mixture of water and toluene, or a mixture of water and 1,2-dimethoxyethane.

9. The method of claim 8, wherein the mixture of water and ethanol, the mixture of water and toluene, and the mixture of water and 1,2-dimethoxyethane, a ratio of water and ethanol, water and toluene, and water and 1,2-dimethoxyethane is 100:1~1:100.

10. The method of claim 1 or claim 2, wherein the step 1) of claim 1 or the step 1) of claim 2 is performed at 60° C.~150° C.

11. The method of claim 1, wherein the oxidant is selenium dioxide or ceric ammonium nitrate.

12. The method of claim 1, wherein the step 2) is performed using any one solvent selected from the group consisting of 1,4-dioxane, dimethylformamide, tetrahydrofuran, methanol and acetonitrile.

13. The method of claim 1, wherein the step 2) is further performed in the presence of an acid.

14. The method of claim 13, wherein the acid is any one selected from the group consisting of hydrochloric acid, nitric acid, sufuric acid, phosphoric acid, acetic acid, p-toluene sulfonic acid (p-TSA), and camphorsulfonic acid (CSA).

15. The method of claim 13, wherein the acid is added in an amount of 0.01~1.0 equivalents.

16. The method of claim 1, wherein the step 2) is performed at 60° C.~150° C.

17. The method of claim 1 or 2, wherein the step 3) of claim 1 or the step 2) of claim 2 is performed at 60° C.~150° C.

18. Any one compound selected from the group consisting of:
- 4-(3-chloropyridin-2-yl)-1-naphthaldehyde,
- N-(3-fluoro-4'-formylbiphenyl-4-yl)methane sulfoneamide,
- 3-(trifluoromethyl)-2,3'-bipyridine-6'-carbaldehyde, and
- 3-chloro-2,3'-bipyridine-6'-carbaldehyde.

* * * * *